United States Patent [19]
Zimmermann et al.

[11] Patent Number: 5,759,824
[45] Date of Patent: Jun. 2, 1998

[54] GENES FOR BUTYROBETAINE/ CROTONOBETAINE-L-CARNITINE METABOLISM AND THEIR USE FOR THE MICROBIOLOGICAL PRODUCTION OF L-CARNITINE

[75] Inventors: Thomas Zimmermann, Naters; Josef Werlen, Ferden, both of Switzerland

[73] Assignee: Lonza, A.G., Gampel/Valais, Switzerland

[21] Appl. No.: 615,191

[22] PCT Filed: Oct. 7, 1994

[86] PCT No.: PCT/EP94/03317

§ 371 Date: Jul. 2, 1996

§ 102(e) Date: Jul. 2, 1996

[87] PCT Pub. No.: WO95/10613

PCT Pub. Date: Apr. 20, 1995

[30] Foreign Application Priority Data

Oct. 8, 1993 [CH] Switzerland ............ 03036/93
Jan. 6, 1994 [CH] Switzerland ............ 00036/94

[51] Int. Cl.$^6$ .............. C12P 13/00; C12N 1/20; C07H 21/04
[52] U.S. Cl. ............. 435/128; 435/252.3; 435/252.33; 435/252.34; 435/320.1; 536/23.1; 536/23.2; 536/23.7
[58] Field of Search ................... 435/128, 189, 435/232, 320, 243, 252.2, 252.3, 252.33, 253.3, 320.1, 252.34; 536/23.2, 23.7

[56] References Cited

U.S. PATENT DOCUMENTS 4,650,759  3/1987  Yozozeki et al. ............ 435/128
5,300,430  4/1994  Shapiro et al. ............ 435/128

FOREIGN PATENT DOCUMENTS 2021869  1/1991  Canada.
2083407  5/1993  Canada.
0122794  10/1984  European Pat. Off..
0457735  11/1991  European Pat. Off..

OTHER PUBLICATIONS

Lindstedt et al., Biochemistry 16, 2181–2188, 1977.
M. Labes et al., Gene, 89, 37–46, 1990.
Amann et al., Gene, 25, 167–178, 1983.
Russell and Bennett, Gene, 20, 231–243, 1982.
Knauf and Nester, Plasmid, 8, 45–54, 1982.
Haas and Itoh, Gene, 36, 27–36, 1985.
Bagdasarian et al., Gene, 26, 273–282, 1983.
Comai et al., Plasmid, 10, 21–30, 1983.
R. Simon et al., Biotechnology, 1, 784–790, 1983.
F. Bolivar et al., Gene, 2, 95–113, 1977.
Cohen et al., 69, Proceedings of the National Academy of Science, 2110–2114, 1972.
Borck et al., Mol. Gen. Genet., 146, 199–207, 1976.
W. Selbitschka et al., Mol. Gen. Genet., 229, 86–95, 1991.
A. C. Y. Chang and S. N. Cohen, J. Bacteriol., 134, 1141–1156, 1978.
W. Selbitschka et al., Appl. Microbiol. Biotechnol., 38, 615–618, 1993.
Kulla et al., Arch. Microbiol., 135, 1–7, 1983.

Primary Examiner—Robert A. Wax
Assistant Examiner—Nashaat T. Nashed
Attorney, Agent, or Firm—Fisher Christen & Sabol

[57] ABSTRACT

An isolated DNA fragment including the genes bcoC, bcoA/B, bcoD coding for the enzymes for L-carnitine biosynthesis in γ-butyrobetaine/crotonobetaine metabolism and, additionally, including the gene bcoT coding for a potential transport protein in γ-butyrobetaine/crotonobetaine metabolism. Also, any vector which includes an isolated DNA fragment including the genes bcoC, bcoA/B, bcoD coding for the enzymes for L-carnitine biosynthesis in γ-butyrobetaine/crotonobetaine metabolism and, additionally, including the gene bcoT coding for a potential transport protein in γ-butyrobetaine/crotonobetaine metabolism. Also, biotechnological process for the production of L-carnitine characterized in that crotonobetaine and/or γ-butyrobetaine is fermented in the presence of a suitable carbon and nitrogen source using a microorgansim and L-carnitine is isolated.

19 Claims, 7 Drawing Sheets

BUTYROBETAINE / L-CARNITINE OPERON
Restriction map

GENES FOR BUTYROBETAINE/ CROTONOBETAINE-L-CARNITINE METABOLISM AND THEIR USE FOR THE MICROBIOLOGICAL PRODUCTION OF L-CARNITINE

This is a national stage application of PCT/EP94/03317 filed on Oct. 7, 1994.

The present invention relates to recombinant genetic material for expression of the genes of butyrobetaine/ crotonobetaine-L-carnitine, microorganisms which contain this recombinant genetic material, and the use of such microorganisms in a biotechnological process for the production of L-carnitine.

L-carnitine is a natural, vitamin-like substance of great importance in human metabolism. In the utilization of fatty acids, L-carnitine is essential as a transmitter substance of the mitochondrial membrane and, thus, as a transporter of metabolic energy. If L-carnitine is synthesized in inadequate amounts by the body, it must be added to the diet to avoid deficiency symptoms. Especially in the diet of infants, who are still unable to biosynthesize their own L-carnitine, L-carnitine is an essential nutrient.

L-carnitine preparations are employed as active constituents of pharmaceutical products. Supplementation with L-carnitine is indicated in the case of carnitine deficiency and other therapeutic indications, especially in cardiac disorders, etc.

The biosynthesis of L-carnitine in higher organisms is known; further functions in and importance for metabolism are objects for intensive research activity. In addition to a metabolic pathway which is described for microorganisms, especially of the genus Pseudomonas (γ-butyrobetainehydroxylase catalysis, Lindstedt et al., Biochemistry 16, 2181–2188, 1977), L-carnitine is formed as a metabolic intermediate of certain microorganisms, e.g. of *Agrobacterium/Rhizobium sp.*.

EP-A-0 158 194 discloses a process for the microbiological production of L-carnitine, starting from, for example, γ-butyrobetaine, in which an L-carnityl dehydrogenase negative production mutant is obtained by means of traditional microbiological selection processes, using which relatively good yields of L-carnitine are already obtained within a reaction time of 20 to 30 hours. A further optimization of this process with respect to the volume/time yields, however, is not possible using this classical microbiological method.

It is, therefore, the object of the present invention to provide a more economical biotechnological process for the production of L-carnitine, in which L-carnitine is obtained in a significantly shorter reaction time with even better yields.

Investigations on γ-butyrobetaine/crotonobetaine metabolism led to the identification of five genes, bcoA/B, bcoC, bcoD, bcoE and bcoT, which code for enzymes of the γ-butyrobetaine/crotonobetaine metabolic pathway and are contained, inter alia, in an operon, the so-called butyrobetaine-L-carnitine operon (bco). In this context the abbreviations have the following meanings bcoA/B: a γ-butyrobetaine-CoA synthetase (bcoA)/ crotonobetaine-CoA synthetase (bcoB) gene, i.e. a unique gene which codes for an enzyme product which has both γ-butyrobetaine-CoA synthetase activity and crotonobetaine-CoA synthetase activity.

bcoc: a γ-butyrobetaine-CoA dehydrogenase gene bcoD: a crotonobetaine-CoA hydrotase gene bcoE: an L-carnityl dehydrogenase gene; and bcoT: a potential gene of the transport system.

It was found that the gene products of the genes bcoA/B, bcoc and bcoD are responsible for the biosynthesis of L-carnitine, while bcoE encodes a carnitine dehydrogenase which causes the degradation of the metabolic intermediate L-carnityl-CoA to betaine. bcoT is presumably a gene which codes for a transport protein of a transport system assigned to butyrobetaine metabolism. This gene is not essential for L-carnitine biosynthesis.

The present invention accordingly relates to DNA fragments and vectors which comprise one or more of the genes bcoc, bcoA/B and bcoD coding for the enzymes for the biosynthesis of L-carnitine in γ-butyrobetaine/ crotonobetaine metabolism and, optionally, additionally the potential transport gene bcoT.

The invention further relates to microorganisms which contain these DNA fragments and/or vectors. The invention further relates to a biotechnological process for the production of L-carnitine using the microorganisms according to the invention.

The designations bcoA/B, bcoc, bcoD and bcoT, as are used here in the description and the claims, comprise, as defined, both the genes of wild-type organisms which code for the enzymes of γ-butyrobetaine/crotonobetaine-L-carnitine metabolism having the abovementioned enzyme activities, in particular the genes of the butyrobetaine-L-carnitine (bco) operon, and their functionally equivalent genetic variants and mutants, i.e., genes which are derived from the genes of the wild-type organisms and whose gene products are essentially unaltered in their biological function. The functionally equivalent genetic variants and mutants, thus, include, for example, base exchanges in the context of the known degeneration of the genetic code, as can be produced, for example, artificially in order to adapt the gene sequence to the preferred codon use of a certain microorganism in which expression is to take place. The variants and mutants further include deletions, insertions and substitutions of bases or codons, to the extent that they leave the gene products of genes modified in this way essentially unchanged in their biological function. Included hereby are, for example, gene sequences which have a high homology, for example higher than 70%, to the wild-type sequences and are able to hybridize with the complement of the wild-type sequences under stringent hybridization conditions, e.g. at temperatures between 50° and 70° C. and at 0.5 to 1.5M salt content.

The term transcription unit as is used here is understood to mean DNA sequences in which genes are arranged in one transcription direction and are transcribed under common transcription control in an uninterrupted transcript, the DNA sequences in addition to the genes additionally having genetic control elements necessary for gene expression, such as, promoters and ribosome binding sites.

The invention is illustrated in greater detail by the following figures.

Figure 1:
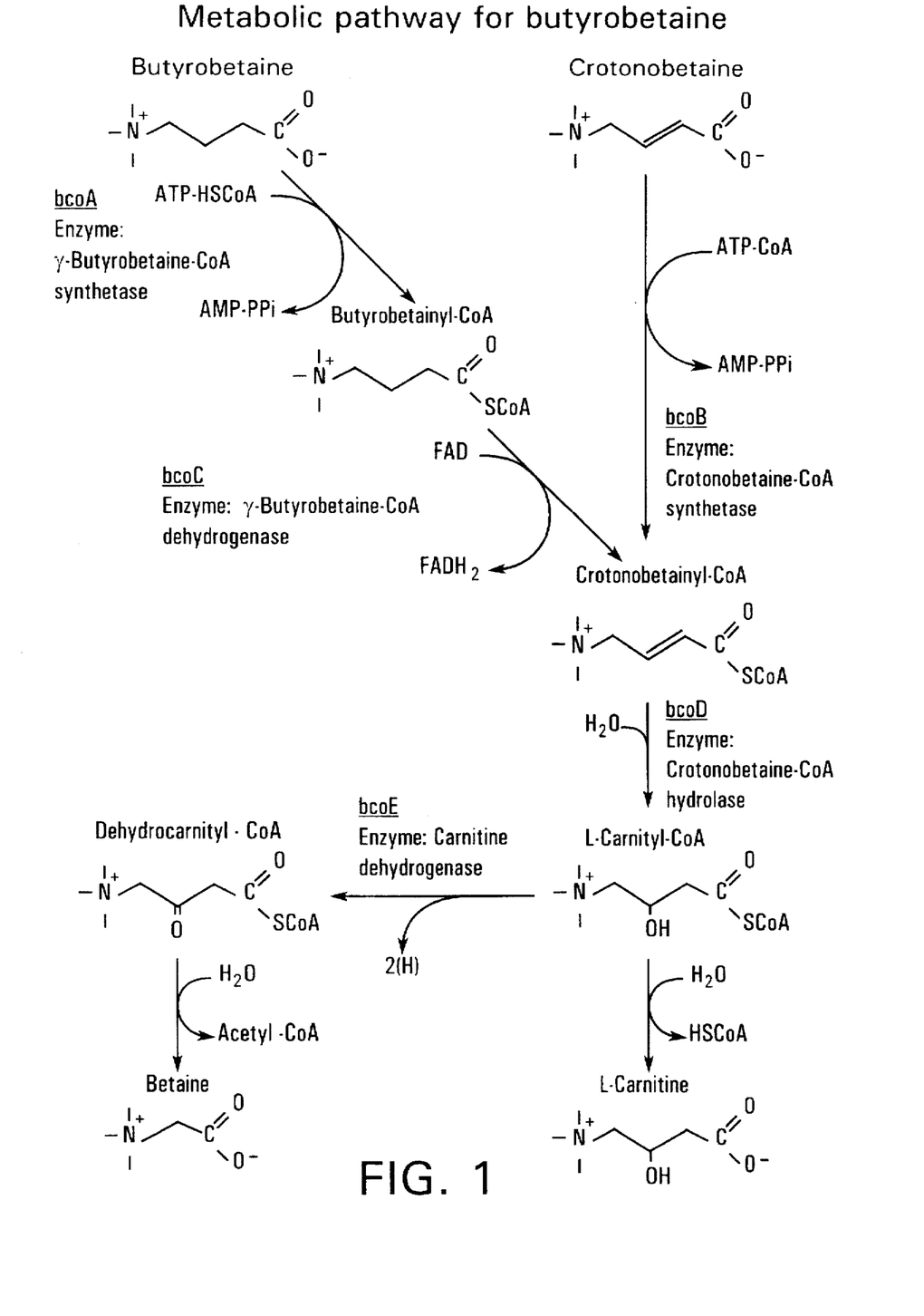
FIG. 1 shows the enzymes of the γ-butyrobetaine- or of the crotonobetaine-L-carnitine metabolic pathway.

The starting matrials used for the isolation of the genes bcoA/B, bcoc, bcoD and bcoT of the γ-butyrobetaine/crotonobetaine-L-carnitine metabolic pathway can be all microorganisms which metabolize butyrobetaine and/or crotonobetaine according to FIG. 1. Examples of suitable strains are microorganisms of the genera Escherichia, Pseudomonas, Agrobacterium, Rhizobium and Agrobacterium/Rhizobium, the latter being preferred. An example of a preferred microorganism of the genus Agrobacterium/Rhizobium is a microorganism of the species *Agrobacterium Rhizobium sp.* HK4 (DSM 2938), as has already been described in EP-A-0 158 194. Those microorganisms are particularly preferably used which are already carnitine dehydrogenase-negative, i.e., for example have no or only a defective bcoE gene (in the following also designated as bcoE'). Examples of preferred carnitine dehydrogenase-negative microorganisms are microorganisms of the species *Agrobacterium/Rhizobium sp.* HK13 (DSM 2903) and HK1331b (DSM 3225), which have already been described in EP-A-0 158 194, or the species *Agrobacterium/Rhizobium sp.* HK1349 (DSM 3944), which is described in EP-A-0 543 344.

The genes bcoA/B, bcoC, bcoD and bcoT of γ-butyrobetaine/crotonobetaine-L-carnitine metabolism can be localized in the chromosome of a microorganism by subjecting the microorganisms, for example, to transposon insertion mutagnesis and thereby labelling the genes of γ-butyrobetaine/crotonobetaine-L-carnitine metabolism with a suitable label, for example of kanamycin (Km) resistance. Mutants labelled in this way, which can no longer utilize intermediates of butyrobetaine metabolism, can then be isolated. In this manner, the genes of γ-butyrobetaine/crotonobetaine-L-carnitine metabolism can be identified and related in their function. The labelled genes can then be cloned and characterized in greater detail using suitable restriction enzymes. The isolation of the intact genes or of the DNA fragments according to the invention can then be carried out starting from a gene bank of a corresponding unmutated microorganism, from which the bco genes or fragments thereof can be isolated and identified in a known manner by hybridization with the cloned genes of the mutagenized strain obtained as above. The genes obtained can then be cloned into the desired vectors and mapped with the aid of restriction enzymes.

Only the genes bcoA/B, bcoc and bcoD are responsible for the biosynthesis of L-carnitine. Accordingly, also only the presence of these genes is necessary for the production of L-carnitine. Depending on the starting conditions selected, for example, the starting material selected or the production strain selected, the DNA fragments and vectors employed in L-carnitine production can contain one or more of the genes of L-carnitine biosynthesis.

In addition to the genes bcoA/B, bcoC and bcoD, the DNA fragments and vectors according to the invention can, if desired, also include the potential transport gene bcoT.

The presence of an L-carnityl dehydrogenase gene, i.e., of a bcoE gene, is undesirable, as in its presence degradation of L-carnitine takes place. The presence of a defective bcoE gene (bcoE'), however, is harmless.

Expediently, the genes for L-carnitine biosynthesis, namely bcoC, bcoA/B and bcoD and optionally the potential transport gene bcoT, for use in the production of L-carnitine, are present together on one DNA fragment or vector molecule, for example preferably in the conventional 5'-3'-direction downstream from the gene-regulatory elements, in the sequence bcoC, bcoA/B and bcoD or bcoC, bcoA/B, bcoD and bcoT and in a single transcription unit defined as above, corresponding to the arrangement in the naturally occurring butyrobetaine-L-carnitine operon. The genes bcoC, bcoA/B, bcoD and bcoT of such a transcription unit can be characterized, for example, by the corresponding sections of the restriction map of FIG. 2.

The transcription or expression of the bco genes expediently takes place under the control of a suitable, preferably strong, promoter. The choice of the promoter depends on the expression conditions desired, for example on whether a constitutive or induced expression is desired, or on the microorganism in which expression is to take place. A suitable promoter is, for example, the promoter $P_{bco}$ of the natural butyrobetaine-L-carnitine operon. If the isolation of the bco genes responsible for L-carnitine biosynthesis takes place, for example, from a microorganism having a defective bcoE gene (bcoE'), advantageously the whole bco operon can, for example, be isolated and cloned with the bcoE' gene and the related gene-regulatory elements from these microorganisms and then employed in suitable microorganisms for the production of L-carnitine. A transcription unit of this type having a mutated bcoE gene, such as can be isolated, for example, from Rhizobium/Agrobacterium HK1349, can optionally also be characterized by the restriction map shown in FIG. 2 if the defect in bcoE is to be attributed, for example, only to a point mutation and does not relate to a restriction cleavage site. Further promoters suitable for expression are, for example, the promoters $P_{Nm}$, $P_{s1}$ (M. Labes et al., Gene, 89, 37–46, 1990), the trp promoter (Amann et al., Gene, 25, 167–178, 1983), the lac promoter (Amann et al., Gene, 25, 167–178, 1983) and the tac promoter, a hybrid of the said trp and lac promoters which can be employed as a constitutive or inducible promoter (Russell and Bennett, Gene, 20, 231–243, 1982).

For use in the production of L-carnitine in a suitable production strain, the DNA fragments according to the invention, which include the said bco genes, preferably together in a single transcription unit, are incorporated, expediently with the aid of known techniques, into known suitable vectors, in particular expression vectors, for example, phages or plasmids. The vectors used can be autonomic and self-replicating vectors or, alternatively, so-called integration vectors. An integration vector is in this context understood to mean a vector, for example a plasmid, which has at least one sequence homologous to the genomic sequence of the recipient strain and allows an insertion of foreign genes into the genome of the recipient strain by homologous recombination with this sequence. Autonomous and self-replicating vectors are preferably used.

Depending on the nature of the vectors selected, the genes for the enzymes of L-carnitine biosynthesis can be expressed in various organisms. Suitable vectors are both vectors having a specific host spectrum and vectors having a broad host spectrum (broad host range) and the integration vectors described above.

Broad host range vectors employed can be all vectors which are suitable for gram-negative bacteria. Examples of such broad host range vectors are pVK100 (Knauf and Nester, Plasmid, 8, 45–54, 1982), pME285 (Haas and Itoh, Gene, 36, 27–36, 1985) and pKT240 (Bagdasarian et al., Gene, 26, 273–282, 1983) or their derivatives. The derivative of pVK100 used can, for example, be pVK1001, the derivative of pME285 used can, for example, be pAZ10 and the derivative of pKT240 used can, for example, be pL032 (as already described in EP-A-0 543 344).

The integration vectors used in the case of Rhizobium Agrobacterium can be vectors based on pACYC184 or pBR322 (Comai et al., Plasmid, 10, 21–30, 1983).

Figure 3:
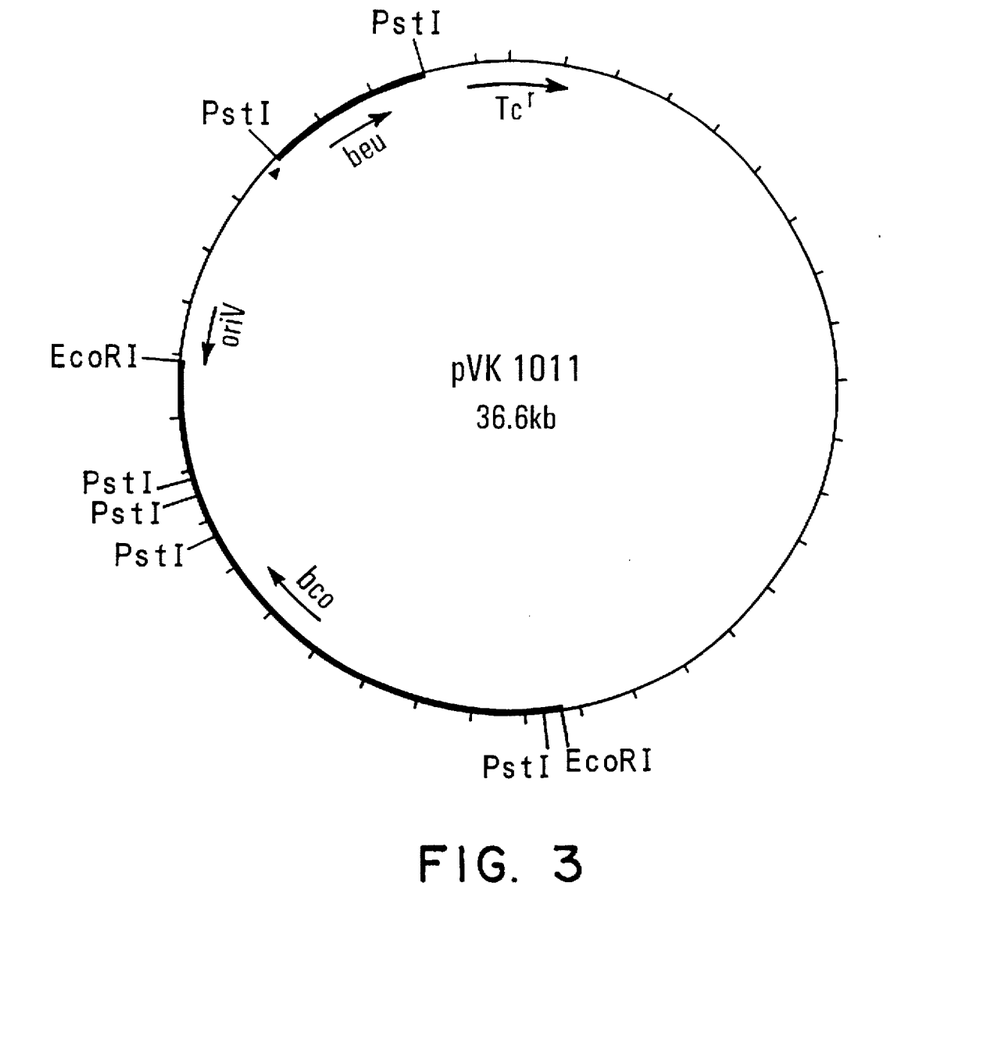
FIG. 3 and FIG. 4 show orasmids pVK 1011 and pAZ101; arrows indicate the position and the orientation of the bco genes and of the beu genes (betaine-utilizing genes; EP-A-0 543 344). The insert portion of the plasmids is shown in bold.
Figure 4:
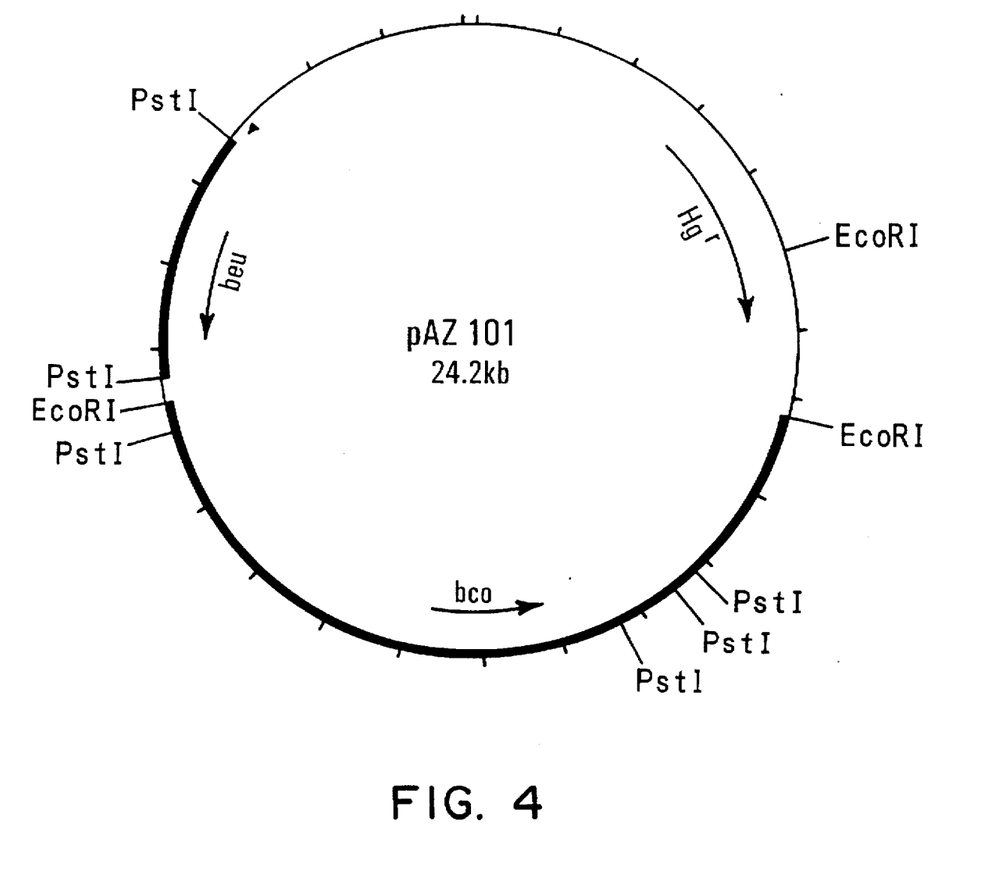
Figure 5:
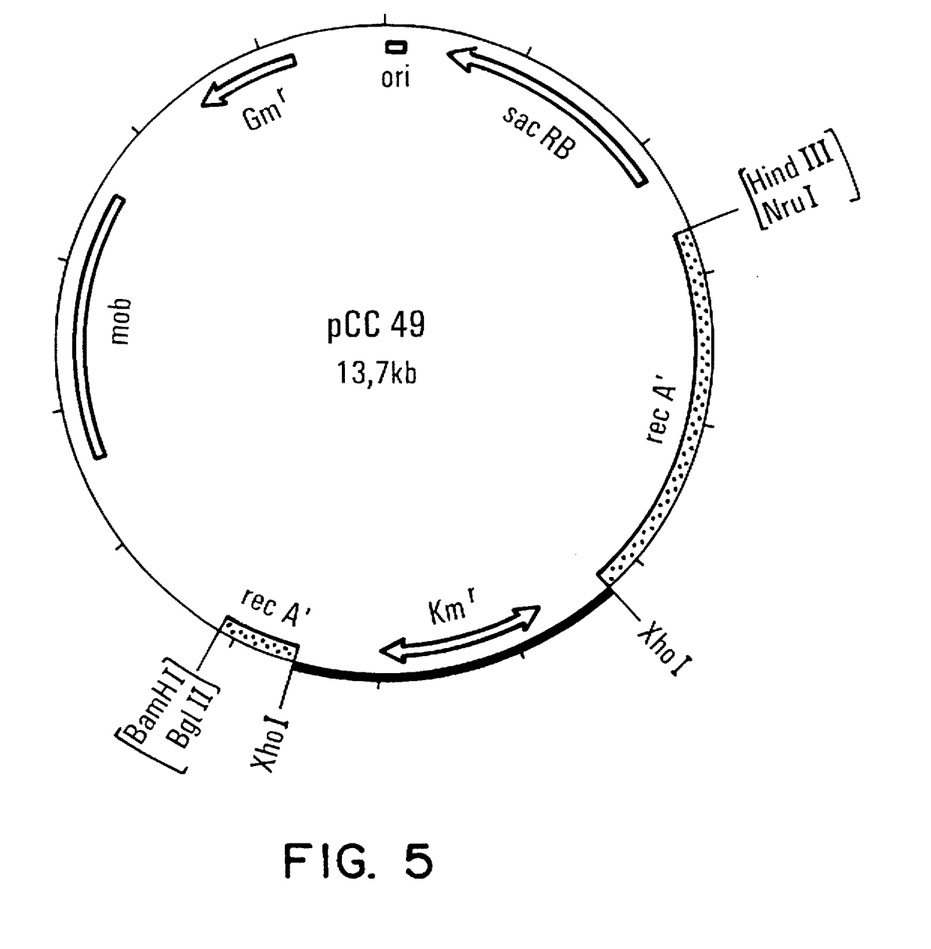
FIG. 5 shows plasmid pCC49 as a possible starting material for the production of an recA host strain.

In this manner, for example, the plasmids pVK100q, pVK101 (FIG. 3), pAZ7, pAZ7::beu, pAZ101 (FIG. 4) and pLO41 were obtained. Plasmid pVK100q was deposited on 16.11.1993 in the German Collection for Microorganisms and Cell Cultures GmbH, D-38124 Braunschweig, Mascheroderweg 1b, in Rhizobium/Aarobacterium HK1349 under the deposit number DSM 8726.

For the production of the production strains for fermentation, i.e., the strains for L-carnitine production, the DNA fragments or vectors according to the invention must be incorporated into the host strains which are desired and are suitable for expression. Expediently, the microorganisms are transformed for this purpose in a manner which is customary and known per se using the vectors containing the DNA fragments according to the invention. The microorganisms can then contain the DNA fragment according to the invention either on a vector molecule or integrated into its chromosome.

Suitable production strains are all microorganisms which are capable of producing L-carnitine from crotonobetaine and/or γ-butyrobetaine and whose capability for the degradation (catabolism) of L-carnitine is completely or partially inhibited. Microorganisms whose L-carnitine catabolism is inhibited are, for example, strains which are carnitine dehydrogenase-negative, i.e. strains in which the carnitine dehydrogenase gene bcoE is switched off, for example, by mutation or deletion, and/or strains which are L,D-carnitine racemase-negative and L-carnitine dehydratase-negative.

Suitable host strains, preferably strains having high substrate and starting material tolerance are, for example, microorganisms of the genera Escherichia, Pseudomonas, Agrobacterium, Rhizobium, Camamonas and Rhizobium/Aarobacterium, the latter being preferred. Microorganism of the species *Rhizobium Agrobacterium sp.* HK13, HK1331b and HK1349 already described above, and also of the species HK1349.4 (as described in EP-A-0 543 344) are particularly preferred.

It was additionally found that the yield of L-carnitine can be improved still further if the capability of the host strain for recombination, i.e., its recombination tendency and recombination frequency, is reduced. A recombination with the vector on the basis of chromosomal homology is restricted thereby. The recombination capability of the host strain can be reduced, for example, in a known manner by specific mutation of its recA gene (recA mutation). Particularly preferred microorganisms which are impaired in their recombination capability are microorganisms of the species *Rhizobium/Agrobacterium sp.*, for example of the strains of the species Rhizobium/Agrobacterium HK1349.49 according to the invention obtained as described below.

Suitable production strains are, thus, for example, microorganisms of the species Rhizobium/Agrobacterium HK1349, HK1349.4 and HK1349.49, in each case containing plasmid pVK100q, pVK1001, pAZ7, pAZ7::beu, pAZ101 or pLO41.

The transformed host strains (production strains) can be isolated from a selective nutrient medium, to which an antibiotic is added against which the strains are resistant owing to a marker gene located on the vector or DNA fragment. If microorganisms according to EP-A-0 543 344 are used as production strains, i.e., microorganisms whose chromosomal gene coding for betaine utilization is mutated and transformed with a plasmid which contains the gene coding for betaine utilization, they can also be selected with respect to betaine utilization. Examples of microorganisms selectable with respect to betaine utilization are the already-mentioned HK1349.4 and HK1349.49, which contain, for example, plasmid pLO41, pAZ101, pAZ7::beu or pVK1011.

The biotechnological production of L-carnitine is carried out using microorganisms which contain the DNA fragments or vectors according to the invention. The process for the production of L-carnitine is carried out by methods known per se, e.g. as described in EP-A-0 158 194, starting from, for example, γ-butyrobetaine in the presence of a suitable carbon and nitrogen source. The carbon and nitrogen source employed can be, for example, glutamate, acetate and betaine, or glycerol and betaine. If the biotechnological production is carried out by means of microorganisms selectable with respect to betaine utilization, betaine is used as the only nitrogen source.

The fermentation and the subsequent isolation of L-carnitine can be carried out analogously to the process described in EP-A-0 158 194.

By variation of the nutrients in the medium and by adapting the fermentation conditions to the particular microorganism in a customary manner, the yield of L-carnitine can be further improved.

EXAMPLE 1

Production of Transposon Insertion Mutants (Tn5) and their Phenotypic Identification The wild-type strain Rhizobium/Aarobacterium HK4 (DSM 2938, EP-B 0 158 194) was made to develop spontaneous resistance to streptomycin (Sm, 1000 μg/ml) by selection pressure. This resistance was demonstrably stable over 50 generations without selection and was used as a selection marker.

0.2 ml of a Tn5 donor culture, of *E. coli* S17-1/pSUP2021 (R. Simon et al., Biotechnology, 1983, 1, 784–790), was mixed with 2 ml of the recipient culture HK4 and centrifuged. The cells were washed in 0.9% saline (NaCl solution) and resuspended in 100 μl of 0.9% saline. The conjugation of the recipient strain with the donor strain was carried out overnight at 30° C. on dry nutrient agar. The harvested cells were plated in dilutions on selection medium for recipient ($Sm^R$) and transposon (neomycin resistance ($Nm^R$))

Tn5 mutants were obtained on nutrient agar using Sm (1000 μlg/ml) and Nm (100 μg)ml). The phenotypic identification of the mutants took place via detection of the non-utilization of the butyrobetaine metabolic intermediates according to FIG. 1 as a carbon (C) source in minimal medium.

EXAMPLE 2

Cloning of the Tn5-labelled DNA Fragments from the HK4 Genome

Isolated genomic DNA from Tn5-mutated HK4 (5 μg) was digested completely with EcoRI (4 U/μg), pBR325 (2.5 μg) (Gene, 1977, 2, 95–113) was treated with alkaline phosphatase after complete digestion by EcoRI. Recombinant hybrid plasmids were obtained after mixing genomic DNA and pBR325 with T4-DNA ligase (0.2 U (units)/μg of DNA) in 400 μl of ligation buffer (20 nM tris-HCl, pH 7.2, 10 mM DTT (dithiothreitol), 10 mM $MgCl_2$, 0.6 nM ATP) and incubation overnight at 12° C.

Aliquots of the ligation mixture were employed for the transformation (Cohen et al., 1972, PNAS 69, 2110–2114) of *E.coli* ED 8654 (Barek et al., Mol. Gen. Genet., 146, 199–207, 1976). Transformants were selected in nutrient medium for their resistance to ampicillin (Ap, 100 μg/ml) and kanamycin (Km, 25 μg/ml). All hybrid plasmids selected carried an HK4 insert which was labelled with Tn5.

Figure 2:
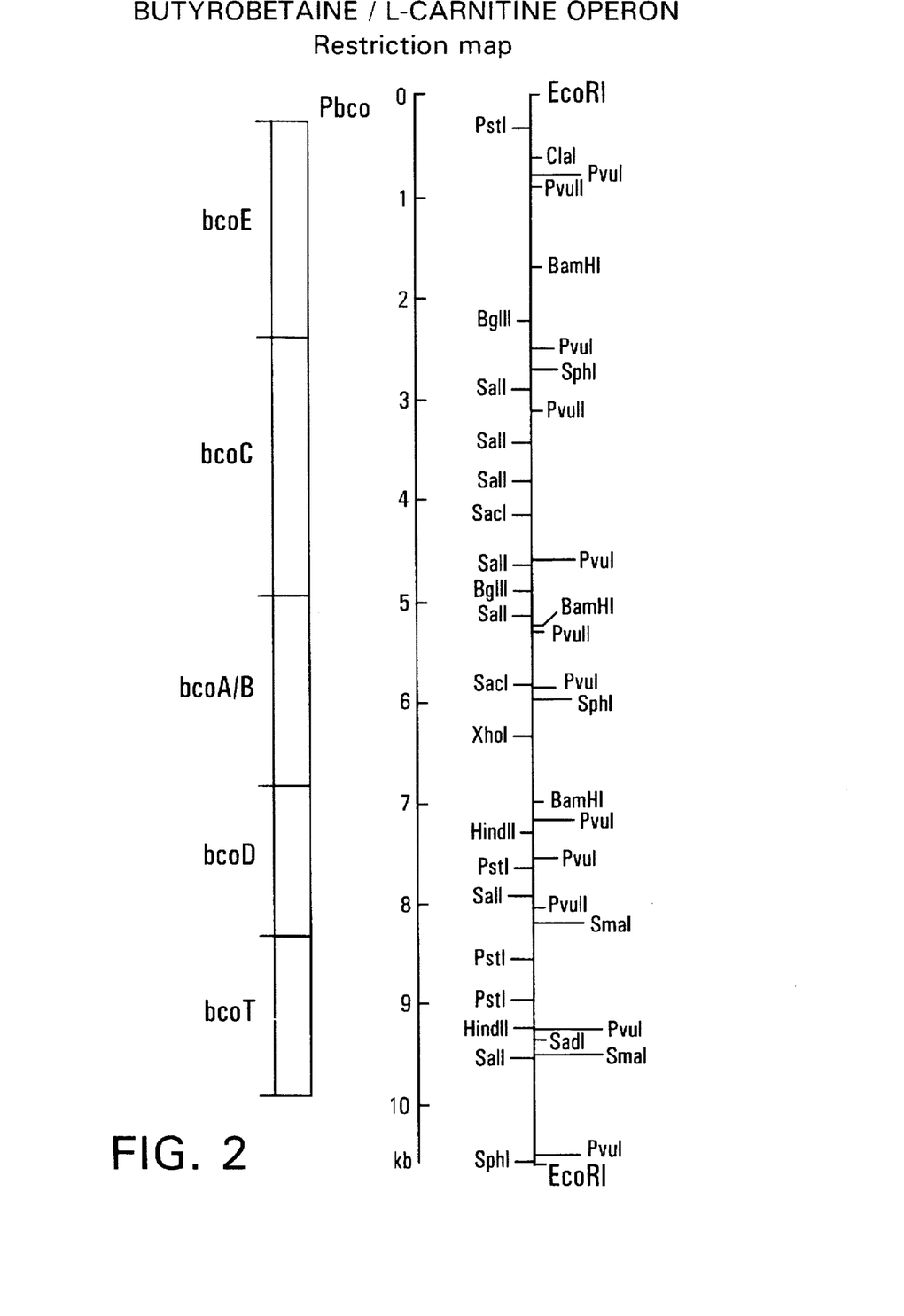
FIG. 2 shows the restriction map of a 10.6 kb DNA fragment from Rhizobium/Agrobacterium having the bco operon.

The inserts were mapped for various restriction enzymes, corresponding to the restriction map in FIG. 2. Comparisons of the restriction maps confirmed the transposon insertion in the same genomic fragment in a series of Tn5 mutants having a different phenotype.

It was possible to confirm this observation by Southern blot hybridization ("Gentechnische Methoden" [Genetic Engineering Methods], edited by S. Bertram and H. G. Gassen, G. Fischer Verlag 1991, 219 f.) of identically cleaved plasmid DNA and subsequent electrophoretic separation. The probes used were subfragments of this cloned DNA from the transposon mutants.

EXAMPLE 3

Setting up a Genomic HK4 Gene Bank in Lambda Phages

In order that DNA can be packaged in lambda phages, it needs a size of 40–52 kb and a "cos site". To set up a genomic HK4 gene bank in lambda phages, the cosmid vector pVK100 (Knauf and Nester, 1982, Plasmid 8, 45–54) was used which is of size 23 kb and thus permits the cloning of DNA fragments between 17–29 kb.

pVK100 was digested with EcoRI, dephosphorylated and ligated with HK4 DNA which was partially digested with EcoRI. The ideal EcoRI concentration for the partial digestion of HK4 DNA was determined by means of test digestion as 0.58 U/μg of DNA or 0.02 U/μg of reaction mixture, 8.5 μg of HK4 DNA being employed in the reaction mixture. The DNA fragments in the size range of greater than 17 kb were isolated from agarose electrophoresis gels. Ligation was carried out in 10 μl volumes containing 100 ng of cosmid vector and 400 ng of passenger DNA. "In vitro packaging" was then carried out corresponding to the protocol of the manufacturer in the mix of Promega Biotec. in the course of 2 hours at 25° C. After transfection of $E.\ coli$ S17-1, selection was carried out for the Km resistance of the cosmid vector. About 5500 colonies (individual clones) were obtained using a batch. The gene bank colonies were stored at −70° C. in 5 batches of about 1000 clones each in freezing medium (nutrient yeast broth, NYB, Oxoid and 50% glycerol). The amplification of the gene bank was carried out using 50 μl each of these batches in 10 ml of NYB overnight culture and portioning.

EXAMPLE 4

Screening of the HK4 Cosmid Gene Bank, Identification of the bco Gene-Carrying Cosmid Clones by Means of Colony Hydridization, Dot Blotting Hybridization or Direct Complementation of HK Mutants It was possible to employ the cloned, Tn5-labelled DNA fragments directly as hybridization probes.

Clones having appropriate DNA sequences exhibited hybridization signals and led to the complementation of the defective gene in each case in the HK4 mutant. Cross-hybridizations of the DNA from various mutants confirmed the "clustering" of several genes of butyrobetaine metabolism on a DNA fragment of 10.6 kb (FIG. 2).

Colony hybridization was carried out in a customary manner (S. Bertram and H. G. Gassen, 1991, ibid, 221f.). Dot blotting was also carried out in a known manner (S. Bertram and H. G. Gassen, 1991, ibid, 217f.).

EXAMPLE 5

Complementation of HK Mutants

After accurate localization of the individual genes of butyrobetaine metabolism taking into account the molecular sizes on the basis of the peptide chains identified, it was possible to achieve complementation of the individual mutants by the particular gene sections.

The particular expression plasmid pVK100::HK-DNA was incorporated via conjugation of $E.\ coli$ S17-1 into Rhizobium/Agrobacterium sp. HK4 strains according to Example 1, which contained mutations for different metabolic steps (see FIG. 1). Selection was carried out against the proline (pro) auxotrophy of the donor and on the antibiotic resistance of the vector ($Km^R Tc$ (tetracycline)$^R$).

EXAMPLE 6

6.1 Cloning of the bco Fragment from Strain HK1349 (DSM 3944) and Derivatives To achieve gene dose effects and productivity increases in the production strain, the bco operon from HK 1349 (DSM 3944, EP-A-0 543 344) was cloned. In this strain, the entire bco operon is contained in complete form, but the first gene, bocE, for carnitine-CoA dehydrogenase is mutated. A DNA fragment having the bco operon and obtained from this strain is thus ideal for productivity increases on account of high copy numbers of expression vectors.

The clonings were carried out in a known manner in $E.\ coli$ S17-1, corresponding to Example 3 of EP-A-0 543 344. For this purpose, the 10.6 kb bco operon was isolated from an HK1349 gene bank and ligated in pVK100. Plasmid pVK100q resulted from this (see construction scheme according to FIG. 6). Selection was carried out in $E.\ coli$ S17-1 on NYB Km (25 μg/ml). The correct insert was identified on HK mutants according to the method described in Example 5. EcoRI-cleaved DNA from HK1349 was separated electrophoretically and the fragments in the size range of 10.6 kb were isolated from the gel. The isolated fragments were ligated in EcoRI-cleaved pVK100. Using this hybrid plasmid mixture, $E.\ coli$ S17-1 (proline auxotroph) was transformed and selected on nutrient agar Km (25 μg/ml). The correct hybrid plasmid clone from the vector and the DNA fragment 10.6 kb in size carrying the bco operon were identified by means of "patch-mating" on a lawn of a butyrobetaine-CoA synthetase-negative mutant (HK4V4) on minimal medium with 0.2% (w/v) butyrobetaine as C and N source. The correct clone was able, after conjugative transfer of this type into the mutant, to complement the cells in the utilization of this C source. The clone pVK100q identified in this way was used directly as a production plasmid or as a reservoir for the DNA fragment having the bco operon for further sub-clonings.

Figure 6:
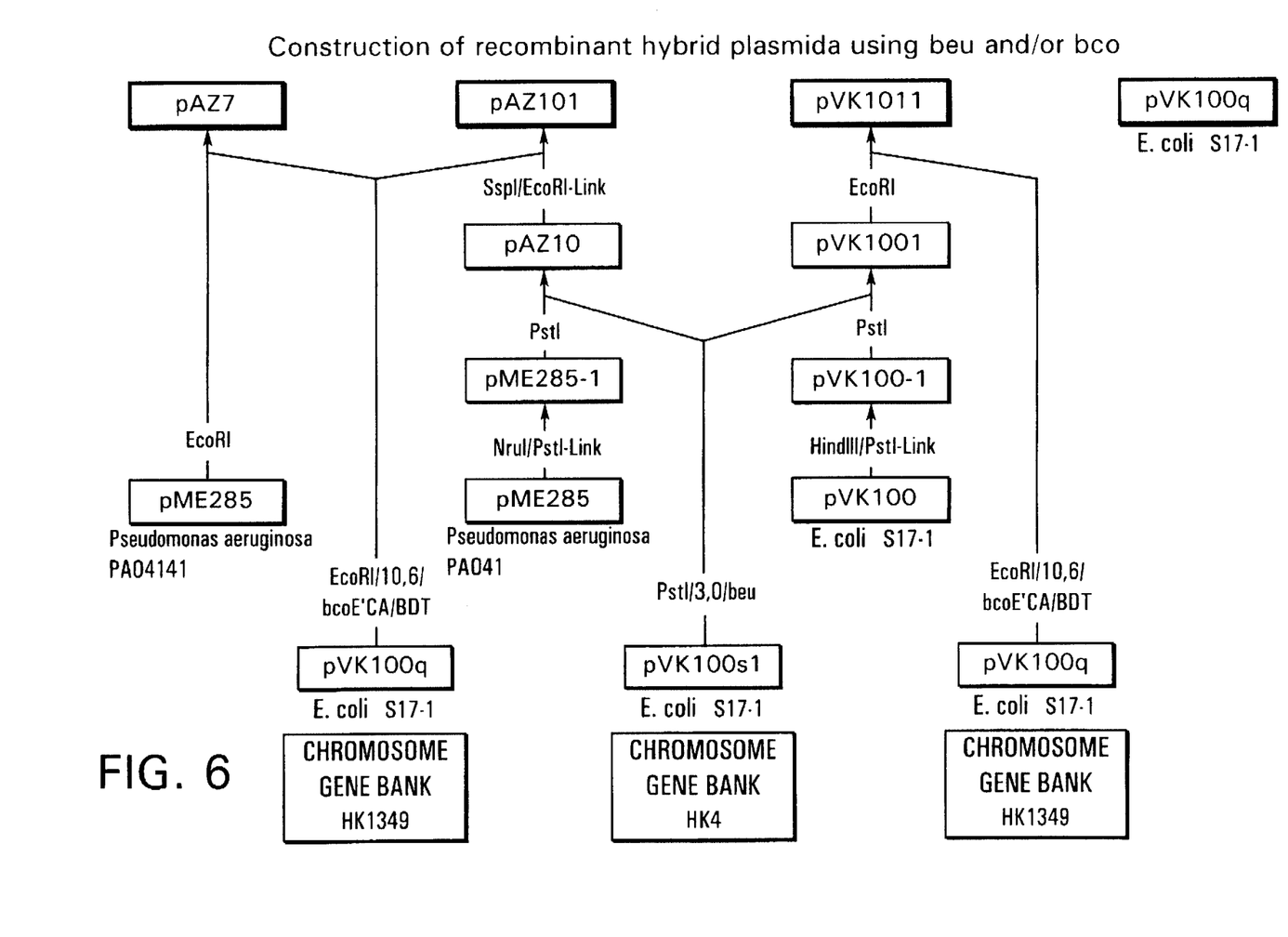
FIG. 6 shows the construction scheme for the plasmids pVK1011, pAZ101, pVK 100q and pAZ7.
Figure 7:
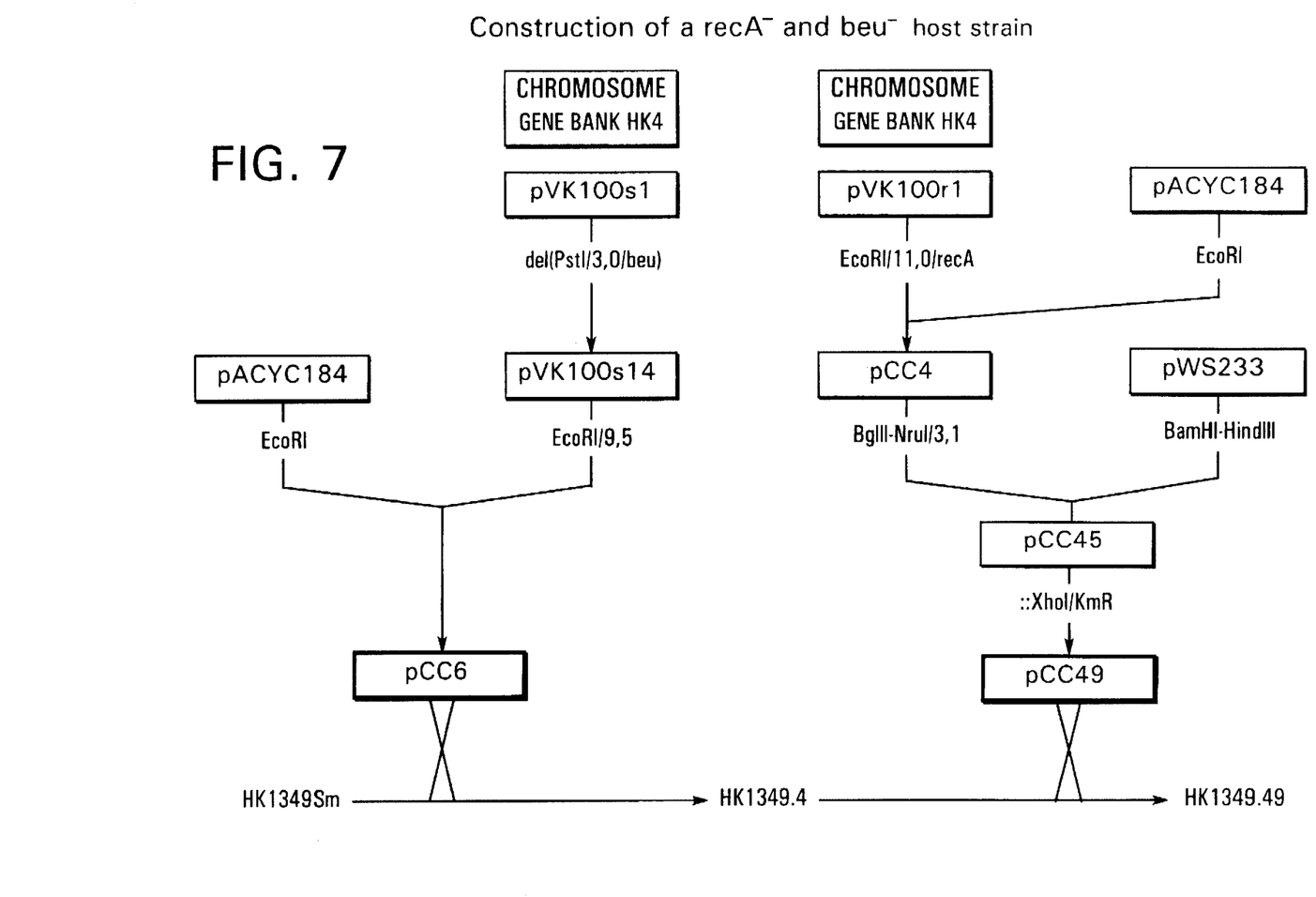
FIG. 7 shows a construction scheme for an recA host strain.

6.2 Construction of pAZ101, pAZ7, pVK1011 and pVK100q, pLO41 and pAZ7::beu pAZ101, pAZ7, pVK1011 an pVK100q were constructed according to the construction scheme of FIG. 6. pLO41 was constructed starting from pLO32 (EP-A-0 543 344) by insertion of the bco genes (10.6 kb EcoRI/EcoRI fragment) and was constructed plasmid pAZ7::beu starting from pAZ7 (FIG. 6) by insertion of the beu genes (3 kb PstI/PstI fragment, EP-A-0 543 344). The corresponding restriction enzymes were employed with 3–5 U/μg of DNA according to the details of the manufacturer. Plasmid pVK100q was obtained by insertion of the bco genes into pVK100 (Knauf and Nester; ibid). The starting plasmid pVK100sl (construction scheme FIG. 6) was obtained by EcoRI deletion clonings of plasmid pVK100s (EP-A-0 543 344).

EXAMPLE 7

Introduction of an recA Mutation into HK1349.4
7.1 Identification of the Gene Bank Clone Coding for recA The genomic HK4 cosmid gene bank was investigated for recA-encoding clones with the aid of the method of colony hybridization (S. Bertam and H. G. Gassen, 1991, ibid, 221f.). The probe used for the hybridization was the cloned recA gene from *Rhizobium leguminosarum* (W. Selbitschka et al., Mol. Gen. Genet., 299, 1991, 86–95). The labelled cosmid clone was isolated, and the EcoRI DNA insert fragments obtained after EcoRI digestion were investigated for recA-homologous sequences by means of Southern blot hybridization against the recA probe (S. Bertram and H. G. Gassen, 1991, ibid, 219f.). The EcoRI fragment labelled in this way was ligated into the vector pVK100, which was cleaved to the same extent. Using the resulting hybrid plasmid pVK100rl, *E. coli* S17-1 cells were transformed for DNA replication.

7.2 Introduction of a Kamaycin Resistance Gene into HK1349.4 for Inactivation of the Chromosomal recA Gene The EcoRI fragment 11.0 kb in size was recloned from pVK100rl into pACYC184 (A. C. Y. Chang and S. N. Cohen, J. Bacteriol., 134, 1978, 1141–1156), which was cleaved with EcoRI.

Corresponding to the restriction map determined, a BglII-NruI-cleaved subfragment 3.1 kb in size, which was labelled against the recA probe in Southern blot hybridization, was cloned into the vector pWS233, which was BamHI-HindIII-cleaved. pWS233 is a "gene replacement" vector and is described in W. Selbitschka et al., Appl. Microbiol. Biotechnol. 38, 1993, 615–618.

An XhoI DNA fragment from Tn5 (pSUP2021, R. Simon et al., Biotechnology, 1, 1983, ibid) which codes for Km resistance was cloned into the XhoI cleavage site of the resulting plasmid pCC45. pCC49 resulted from this. Analogously to the procedure of W. Selbitschka et al., 1993, ibid, a "gene replacement" was carried out in the following manner:

3 ml of exponential HK1349.4 culture were combined with 1 ml of exponential donor culture (S17-1/pCC49), centrifuged and washed with 0.9% NaCl solution. The cells were incubated at 30° C. overnight on nutrient agar in 50 μl of NYB. The cells, which were resuspended in 0.9% NaCl solution, were then applied in a suitable dilution to selective media. Transconjugants of the Sm-resistant recipients HK1349.4 were obtained on nutrient agar using Sm (1000 μg/ml) and Nm (150 μg/ml) and showed sensitivity to 5% sucrose in the complex medium corresponding to the genes sacRB on the "replacement" vector.

Double recombinations were obtained with a low frequency ($10^{-8}$) after the culturing of the selected transconjugants without selection pressure on nutrients agar: After about 1 week it was possible to isolate cells which tolerated 5% sucrose in the medium, remained Nm-resistant but had become gentamycin (Gm)-sensitive again (vector marker).

This phenotype confirms the allelic marker exchange and points to an recA mutation in HK1349.4. The typical phenotype (e.g. UV sensitivity etc.) of recA mutants can be observed.

In the strain HK1349.49 obtained in this way, the tendency of chromosomal integration of plasmids with homologous sequences (homologous recombination) is clearly reduced. The strain is, therefore, a highly suitable host for the hybrid plasmids shown in Example 6.2.

EXAMPLE 8

Biotransformation

The biotransformation was carried out in shaker flasks (100 ml) using N-free minimal medium (MM; Kulla et al., Arch. Microbiol., 1983, 135, pp. 1–7), containing 0.2% (w/v) of γ-butyrobetaine (starting material) and, as a C source, 0.4% (w/v) of glycerol. As a N source and an additional C source, 0.2% (w/v) of L-glutamate (with strains negative in betaine utilization) or 0.2% (w/v) of betaine was added.

The production strains employed were the strains according to the invention HK1349.4/pLO41, HK1349.4/pVK1011, HK1349.4/pAZ7::beu, HK1349.4/pAZ101, HK1349/pVK100q and HK1349/pAZ7.

The results are compiled in the Table shown below in comparison with the HK13 derivatives HK1349 (DSM 3944) and HK1349.4 known from EP-A-0 543 344.

The formation of L-carnitine from γ-butyrobetaine was determined by the DTNB (5.5'-dithiobis(2-nitrobenzoate) method described in Bergmeyer (H. K. Bergmeyer, 1974, Methoden der enzymatischen Analyse [Methods of Enzymataic Analysis], Verlag Chemie, Weinheim, 1810 f.).

| Strains | Medium MM & Glycerol | Spec. activity mmol/l/h/OD |
|---|---|---|
| HK1349 (not according to the invention) | & betaine | 0.24 |
| HK1349/ pVK100q | & betaine | 0.36 |
| HK1349/ pAZ7 | & betaine | 0.49 |
| HK1349 (not according to the invention) | & L-glutamate | 0.14 |
| HK1349.4 (not according to the invention) | & L-glutamate | 0.11 |
| HK1349.4/ pLO41 | & L-glutamate | 0.29 |
| HK1349.4 (not according to the invention) | & ammonium | 0.12 |
| HK1349.4/ pVK1011 | & betaine | 0.54 |
| HK1349.4/ pAZ7::beu | & betaine | 0.47 |
| HK1349.4/ pAZ101 | & betaine | 1.08 |

We claim:

1. An isolated DNA fragment comprising one or more of the genes bcoC, bcoA/B and bcoD for L-carnitine biosynthesis, which code for a γ-butyrobetaine-CoA dehydrogenase (bcoC), a γ-butyrobetaine/crotonobetaine-CoA synthetase (bcoA/B) or a crotonobetaine-CoA hydrotase (bcoD), the genes bcoC, bcoA/B and bcoD and optionally bcoT are derived from microorganisms of the genera Rhizobium/Agrobacterium, said DNA fragment being selected from the group consisting of:

(a) a 10.6 kb EcoRI fragment as inserted in plasmid pVK100q, deposited in Rhizobium/Agrobacterium 1349 under the deposit number DSM 8726, or a subfragment, said subfragment comprising one or more of the genes bcoC, bcoA/B and bcoD, and (b) a fragment which hybridizes under stringent conditions to the 10.6 kb EcoRI fragment wherein the stringent hybridization conditions are under temperatures between 50° and 70° C. at 0.5 to 1.5M salt content and code for enzymes having the activities of γ-butyrobetaine-CoA dehydrogenase (bcoC), of a γ-butyrobetaine/crotonobetaine-CoA synthetase (bcoA/B), and/or of a crotonobetaine-CoA hydratase (bcoD), the genes γ-butyrobetaine-CoA dehydrogenase (bcoC), γ-butyrobetaine/crotonobetaine-CoA synthetase (bcoA/B) and crotonobetaine-CoA hydratase (bcoD) being derived from microorganisms of the genera Rhizobium/Agrobacterium.

2. The DNA fragment according to claim 1, additionally comprising the gene bcoT assigned to γ-butyrobetaine/crotonobetaine metabolism.

3. The DNA fragment according to claim 2, wherein the genes are operatively linked with the genetic control elements necessary for expression.

4. The DNA fragment according to claim 3, wherein the genes of L-carnitine biosynthesis are arranged in the sequence bcoc, bcoA/B and bcoD or, if appropriate, bcoC, bcoA/B, bcoD and bcoT and are present as a single transcription unit.

5. The DNA fragment according to claim 4, wherein the gene-regulatory element comprises the promoter of the natural bco operon, $P_{bco}$.

6. The DNA fragment according to claim 4, wherein the genes bcoC, bcoA/B, bcoD and bcoT are characterized by the restriction map of FIG. 2.

7. The DNA fragment according to claim 1, wherein the genes are operatively linked with the genetic control elements necessary for expression.

8. The DNA fragment according to claim 1, wherein the genes of L-carnitine biosynthesis are arranged in the sequence bcoC, bcoA/B and bcoD or, if appropriate, bcoC, bcoA/B, bcoD and bcoT and are present as a single transcription unit.

9. The DNA fragment according to claim 4, wherein the gene-regulatory element comprises the promoter of the natural bco operon, $P_{bco}$.

10. The DNA fragment according to claim 1, wherein the genes bcoC, bcoA/B, bcoD and bcoT are characterized by the restriction map of FIG. 2.

11. A vector, comprising a DNA fragment according to claim 1.

12. The vector according to claim 11, namely plasmid pVK100q, as deposited in Rhizobium/Agrobacterium HK 1349 under the deposit number DSM 8726, plasmid PVK 1011, as characterized by the restriction map according to FIG. 3, and plasmid pAZ101, as characterized by the restriction map according to FIG. 4.

13. A recombinant microorganism, comprising a DNA fragment or a vector according to claim 1.

14. A microorganism according to claim 13, wherein the capability for the catabolism of L-carnitine of said microorganism is completely or partially inhibited.

15. The microorganism according to claim 13, wherein the capability for recombination of said microorganism is impaired.

16. The microorganism according to claim 13, wherein said microorganism is selected from microorganisms of the genera Escherichia, Pseudomonas, Agrobacterium, Rhizobium, Comamonas and Rhizobium/Agrobacterium.

17. Microorganism Rhizobium/Agrobacterium HK 1349, comprising plasmid pVK100q, as deposited under the deposit under DSM 8726, plasmid pVK1011, as characterized by the restriction map according to FIG. 3, or plasmid pAZ101, as characterized by the restriction map according to FIG. 4, and genetic variants and mutants derived from such microorganisms having the capability for L-carnitine biosynthesis.

18. Microorganism Rhizobium/Agrobacterium HK 1349.4, comprising plasmid pVK100q, as deposited in Rhizobium/Agrobacterium HK 1349 under the deposit number DSM 8726, plasmid pVK1011, as characterized by the restriction map according to FIG. 3, or plasmid pAZ101 as characterized by the restriction map according to FIG. 4, and genetic variants and mutants derived from such microorganisms having the capability for L-carnitine biosynthesis.

19. A biochemical process for the production of L-carnitine, comprising -fermenting crotonobetaine and/or γ-butyrobetaine in the presence of a suitable carbon and nitrogen source by means of a microorganism according to claim 13, whereby L-carnitine is produced, and isolating the L-carnitine.

* * * * *